(12) United States Patent
Adjanohoun et al.

(10) Patent No.: US 11,641,847 B2
(45) Date of Patent: May 9, 2023

(54) IN-OVO INJECTION DEVICE

(71) Applicant: NECTRA, Pacé (FR)

(72) Inventors: Ephrem Adjanohoun, Pacé (FR); Jean Claude Yvin, Plougoulm (FR)

(73) Assignee: NECTRA, Pacé (FR)

( * ) Notice: Subject to any disclaimer, the term of this patent is extended or adjusted under 35 U.S.C. 154(b) by 525 days.

(21) Appl. No.: 16/651,999

(22) PCT Filed: Oct. 2, 2018

(86) PCT No.: PCT/FR2018/052426
§ 371 (c)(1),
(2) Date: Mar. 27, 2020

(87) PCT Pub. No.: WO2019/069012
PCT Pub. Date: Apr. 11, 2019

(65) Prior Publication Data
US 2020/0260696 A1    Aug. 20, 2020

(30) Foreign Application Priority Data

Oct. 3, 2017 (FR) ........................................ 1759249

(51) Int. Cl.
*A01K 45/00* (2006.01)
*C12M 3/10* (2006.01)

(52) U.S. Cl.
CPC ........... *A01K 45/007* (2013.01); *C12M 21/10* (2013.01)

(58) Field of Classification Search
CPC ............................. A01K 45/007; C12M 21/10
See application file for complete search history.

(56) References Cited

U.S. PATENT DOCUMENTS

| 1,213,001 | A | * | 1/1917 | Philips | A61M 25/0606 |
| | | | | | 128/207.29 |
| 3,377,989 | A | | 4/1968 | Sandhage et al. | |
| 3,616,262 | A | * | 10/1971 | Coady | C12M 21/10 |
| | | | | | 134/48 |
| 4,903,635 | A | * | 2/1990 | Hebrank | B65G 47/915 |
| | | | | | 435/303.1 |
| 5,056,464 | A | * | 10/1991 | Lewis | C12M 41/48 |
| | | | | | 119/6.8 |
| 5,136,979 | A | * | 8/1992 | Paul | A61D 19/04 |
| | | | | | 119/6.8 |
| 6,286,455 | B1 | * | 9/2001 | Williams | A01K 45/007 |
| | | | | | 119/6.8 |

(Continued)

FOREIGN PATENT DOCUMENTS

WO    2007/024952 A2    3/2007

*Primary Examiner* — Ebony E Evans
(74) *Attorney, Agent, or Firm* — H&I Partners; C. Andrew Im; Jean-Christophe Hamann

(57) ABSTRACT

A device to inject a composition into an egg includes a guide member, a first locking member and a second locking member. The guide member includes an outer casing secured to the injection needle and an inner casing which can move in translation inside the outer casing. The inner casing connected to the trocar and comprising a cup configured to bear on the upper part of the egg. The first locking member configured to block the movement of the trocar. The second locking member configured to block the movement of the injection needle inserted into the trocar.

12 Claims, 4 Drawing Sheets

(56) References Cited

U.S. PATENT DOCUMENTS

| | | | | |
|---|---|---|---|---|
| 6,499,428 | B1* | 12/2002 | Prindle | A01K 45/007 119/6.8 |
| 6,981,470 | B2* | 1/2006 | Gross | A01K 45/007 119/323 |
| 7,083,208 | B2* | 8/2006 | Ilich | B08B 9/00 294/64.2 |
| 8,297,227 | B2* | 10/2012 | Breuil | A01K 45/007 119/6.6 |
| 8,336,491 | B2* | 12/2012 | Yvin | A01K 45/007 119/6.6 |
| 9,539,382 | B2* | 1/2017 | Nelson | A61M 25/0023 |
| 10,618,741 | B2* | 4/2020 | Schnupper | A23L 15/00 |
| 2006/0075973 | A1* | 4/2006 | Wolfe | A01K 45/007 119/6.8 |

* cited by examiner

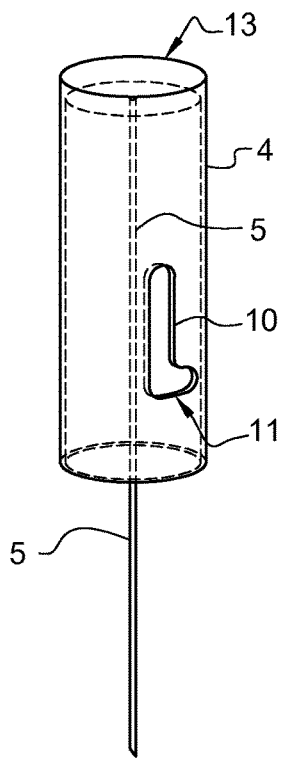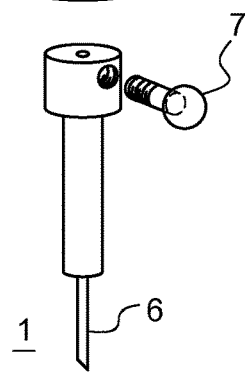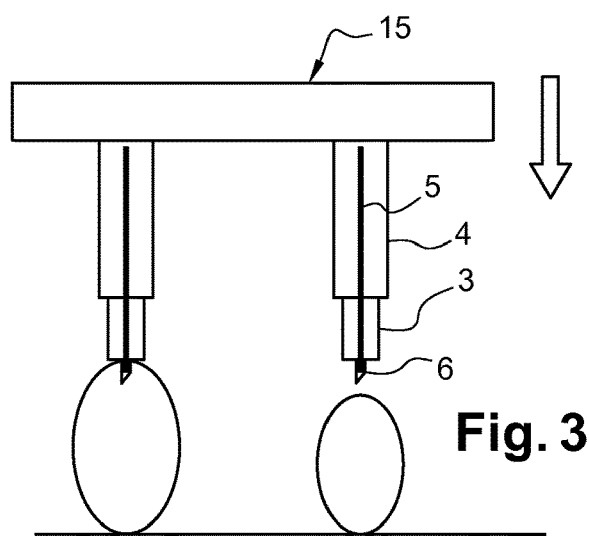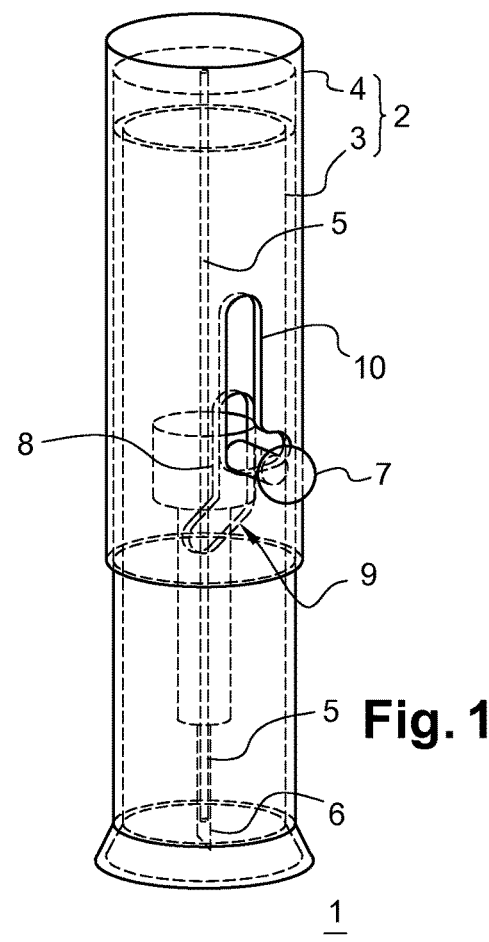

IN-OVO INJECTION DEVICE

RELATED APPLICATIONS

This application is a § 371 application of PCT/FR2018/052426 filed Oct. 2, 2018, which claims priority from French Patent Application No. 17 59249 filed Oct. 3, 2017, each of which is incorporated herein by reference in its entirety.

FIELD OF THE INVENTION

The present invention relates to the field of the injection of compositions into eggs through the shell, also known as in-ovo injections, and in particular relates to a device for injecting compositions into eggs, and more particularly bird eggs such as poultry eggs.

BACKGROUND OF THE INVENTION

The injection of compositions into fertilised eggs allows the embryos to undergo preventive or curative treatment. The injected compositions are, for example, vaccines, antibiotics, dietary supplements, microorganisms and/or components intended to reduce mortality, improve embryonic development, produce vaccines or carry out analyses. Such a technique can also be useful for injecting substances into sterile eggs, for example with a view to adding preservatives, or for collecting egg samples through the shell, etc.

Such injections are generally carried out by means of devices of the prior art including an injection head positioned so as to penetrate the eggs to be treated via one of the ends thereof.

In this context, one known approach described in the U.S. Pat. No. 3,377,989 implements a machine for the automatic in-ovo injection of biological material including a fixed needle, borne by a retractable protective casing positioned on a support which is itself slightly movable, and intended to puncture the shell and inject the in-ovo solution therein by abutment of the egg against the needle. The main drawback of such a technique is that although the support is movable and built into a spring in order to dampen the movements thereof, it is difficult to control the penetration depth of the needle in the egg, which causes irreversible injuries to the embryo when the needle penetrates the egg to inject the in-ovo solution therein. This technique is also relatively unreliable since the needle often becomes clogged by a fragment of shell during puncture, which fragment could be driven in full or in part deep within the interior of the egg during a new injection, thus causing potential contamination of the other embryos. Moreover, such a technique does not allow the impact velocity of the needle, and/or of the remainder of the injection head, against the shell to be precisely controlled, which causes numerous losses resulting from egg breakages.

Another developed approach, also known in the prior art and described in the patent application WO2007/024952, implements an injection system including a pump connected to a needle, which needle is mounted such that it slides inside a punch, intended to puncture the egg, before the sliding of the needle towards the centre of the egg. Such a technique, although reducing the impact of the injection tool and removing the pieces of shell blocked in the punch, does not allow the penetration depth of the punch inside the egg, or the penetration depth of the injection needle to be controlled. More specifically, since the size of the eggs is variable, the injectors fastened to a common support undergo vertical translation during the puncture and injection phases, the punch and the injection needle penetrate deeper into large eggs and shallower into small eggs, the punch can thus descend as far as the more sensitive parts of the egg, and the path of the injection needle can thus be too long and could injure the embryo.

OBJECT AND SUMMARY OF THE INVENTION

In the remainder of the present description and in the context of the present invention, the term "trocar" will be used to denote a means of puncturing the egg in which an injection needle must slide.

The present invention intends to overcome the problems in the prior art and thus relates to a device for injecting a composition into an egg, including a trocar comprising a tubular body and an injection means, said device comprises:
  a guide member comprising a first casing, known as an outer casing, secured to the needle, and a second casing which can move in translation inside the outer casing, known as an inner casing, connected to the trocar and having a cup intended to bear on the top part of an egg;
  a first locking means suitable for blocking the movement of the trocar; and
  a second locking means suitable for blocking the movement of the injection needle in configurations in which the needle is retracted inside the trocar.

The trocar is connected to the inner casing, that is to say that the trocar is either fastened to the inner casing, or that the trocar engages with this casing in configurations of the guide member where the trocar is connected either directly or indirectly to the inner casing while bearing thereagainst. One end of the trocar intended to come into contact with an egg to be treated is cut, for example substantially in a bevel shape, so as to allow for easier puncturing of the shell.

The injection means is advantageously an injection needle for injecting a liquid substance, known as a solution, by penetrating the egg to a controlled depth. The injection means is advantageously mounted such that it slides at least partially inside said tubular body of the trocar between a position in which the injection end thereof is fully retracted inside the tubular body, and a position in which the injection end thereof projects outside of the tubular body of the trocar.

The injection means can alternatively be a nozzle allowing for the injection of at least one gaseous substance, and/or the dispensing of at least one solid body which must be either propelled inside the egg from the outside via the tubular body of the trocar, or directly inserted into the area of interest to be treated in the egg. Such a nozzle can operate, for example, using a gas propellant for emitting a jet.

Thanks to such a device, the trocar and the injection needle can be locked and unlocked asynchronously. The device according to the invention further allows the displacement and path of the trocar and of the needle to be precisely controlled during the steps of puncturing the shell and injecting the composition into the egg. During the puncture phase, the pressure exerted by the injector on the shell of the egg is only applied to the trocar while simultaneously locking the injection needle in the vertical position.

The guide member of the device according to the invention advantageously includes:
  a first grooving made on the outside face of the inner casing and a second grooving made on the inside face of the outer casing, the first and the second groovings extend longitudinally in the guide member and substantially facing one another, the first grooving comprises the first locking means including a first bend positioned at one of the ends of the first grooving, the second grooving comprises the second locking means having a bend, referred to as a second bend, positioned at one of the ends thereof; and a bonding stud mounted such that it slides both inside the first and the second grooving;

the first bend being configured for locking the bonding stud while being free to slide inside the second grooving and capable of bearing against one end of the second grooving; and the second bend being configured for blocking the bonding stud while being free to slide inside the first grooving and capable of bearing against one end of the first grooving.

The term "bend" is understood in the context of the invention to denote a notch which extends at one end of the linear part of greatest length of a grooving.

Such a double-grooving system allows the displacement of the two casings in the guide member to be precisely controlled and provides for blocking with damping thanks to a gradual abutment in the bends. The two groovings are substantially facing one another, they are not necessarily perfectly aligned radially relative to the axis of the guide member, and can be offset relative to one another. The bends are positioned as follows: by sliding the inner casing inside the outer casing, the recess of the first bend extends radially relative to the axis of the guide member in the slot of the second grooving. Similarly, by sliding the inner casing inside the outer casing, the recess of the second bend extends radially relative to the axis of the guide member in the slot of the first grooving. By positioning the in-ovo injection device vertically with the tip of the needle (when the injection means is a needle) facing downwards: the trocar can be lowered while blocking the displacement of the injection means, and conversely, the injection means can be lowered while blocking the displacement of the trocar. After the trocar has punctured the shell and penetrated the interior of the egg to a defined depth, the pressure thereon disappears, only the distal end of the injector applies a force to the top part of the egg, which results in locking the vertical position of the trocar in the egg and in unlocking the injection means, thus allowing the penetration depth of the trocar inside the egg to be limited and defined, and allowing the injection means to be lowered into the egg at a low velocity.

The first grooving advantageously passes through the inner casing and the bonding stud is fastened, on the one hand, by one end to the trocar and passes through, on the other hand, the first grooving while being housed inside the second grooving via the other end thereof. The bonding stud is mounted on the trocar and opens out into the second grooving of the outer casing so as to provide a bearing point for the trocar connected to the two casings for improved holding. Thus, the path of the trocar can end, whereas the injection means, capable of moving inside the trocar, can in turn be lowered until the guide member occupies a configuration wherein the movements of the inner casing relative to the outer casing are all blocked.

The second grooving is advantageously penetrating and is passed through by the bonding stud, which includes a head adapted for engaging with the outer edges of the second grooving; the head of the bonding stud is, for example, a bevelled bolt head.

According to other embodiments, the second locking means advantageously includes, on the one hand, a first magnet positioned on the outside face of the inner casing, and on the other hand, a second magnet positioned on the inside face of the outer casing, said first and second magnets being positioned facing one another in the guide member in a configuration of the guide member known as a puncturing configuration. This double-magnet system allows the casings of the guide member to be displaced relative to one another without sudden movements or jolts. As long as the shell of the egg has not been punctured with penetration of the trocar inside the egg, the injection means is held immobile in the retracted position. The magnetic force F1 exerted between the two magnets is greater than the force F2 required to puncture the shell of the egg, but is less than the bearing force F3 of the cup when in contact with the shell of the egg. As a result, the translation of the outer casing relative to the inner casing is only possible when the cup bears against the shell of the egg and when the trocar has penetrated the egg to the desired depth.

Advantageously, the first locking means of the device described hereinabove is formed by a rigid connection of the trocar to the cup. The cup and the trocar can, for example, be made in one piece by moulding.

Advantageously, the device according to the invention comprises a third locking means capable of blocking the displacement of the injection means in a configuration of the guide member for which the injection means projects outside of the trocar, known as an injection configuration. Thus, the device according to the invention not only allows the insertion depth of the trocar to be controlled and the injection means to be injected, for example, a needle to be injected into the egg at the right time, but also allows the injection depth in the egg to be precisely controlled.

Advantageously, the outer casing includes a bottom and the third locking means comprises said bottom, a border of the inner casing being provided so as to abut against said bottom in the injection configuration. Thus, in the configuration of the guide member wherein all movements of the inner casing relative to the outer casing are blocked, that is to say in the injection configuration, the path of the injection means inside the egg is controlled by the position of the bottom and/or the length of the outer casing, or of the inner casing which must abut against the bottom.

Advantageously, in the device according to the embodiments described in the context of the invention including said first and second groovings, the third locking means is the end of the second grooving opposite that including the first bend. Thus, the bonding stud blocked in the first bend slides in the second grooving and ends its journey in the aforementioned end of the second grooving in order to block the lowering of the injection means into the egg (injection configuration). The path of the needle can be precisely adjusted as a function of the length of the second grooving.

For all of the embodiments described hereinabove in the context of the invention, the inner casing and the outer casing advantageously have a substantially cylindrical shape. Casings having square or triangular sections, etc. can also be implemented. However, circular sections which are easier to produce or resize after manufacture are preferred.

The present invention further relates to a method for the in-ovo injection of compositions, implementing devices such as that described in the context of the invention and comprising the steps of:

starting the compression of the guide member which occupies a first configuration wherein the bonding stud is housed inside the second bend and the injection means is fully retracted;

maintaining compression and subsequently the sliding of the outer casing relative to the inner casing with displacement of the bonding stud in the first grooving until the cup becomes positioned on the top part of an egg according to a second configuration of the guide member;

continuing to compress the guide member in order to puncture the shell by the trocar;

maintaining the compression of the guide member until the egg is punctured and until the guide stud is blocked in the first bend in order to block the displacement of the trocar; and further compressing the guide member to cause the bonding stud to slide inside the second grooving and the injection means to be lowered until the device occupies the injection configuration.

The displacement of the bonding stud inside the first grooving results, at the end of its path, in the sliding of the bonding stud inside the first bend. The successive steps of this sliding of the bonding stud in the first bend cause the trocar to rotate. This rotation of the trocar results in reducing the transverse downwards bearing of the trocar which has already punctured the egg. This rotation of the trocar thus releases the pressure applied to the egg, which prevents the shell of the egg from being broken or cracked.

The present invention further relates to another method for the in-ovo injection of compositions, implementing other devices such as that described in the context of the invention and comprising the steps of:

positioning the trocar on the top part of an egg;

pressurising the guide member on the top part of the egg which occupies the puncturing configuration wherein said first and second magnets are positioned facing one another in the guide member until the egg is punctured;

maintaining compression until the magnetisation between the first magnet and the second magnet is broken, and subsequently until the sliding of the outer casing relative to the inner casing, which results in the lowering of the trocar into the punctured egg until the cup is positioned on the top part of said egg; and further compressing the guide member to cause the injection means to be lowered until the guide member occupies the injection configuration.

BRIEF DESCRIPTION OF THE DRAWINGS

The following detailed description presents the embodiments of the present invention for illustrative purposes only and must not be interpreted as limiting in any way, with the accompanying figures thereof, in which:

FIG. 1 shows a transparent profile view of an injection device according to the invention in order to view the interior of the device;

FIG. 2 shows a profile view of an injection device according to the embodiment shown in FIG. 1, in another configuration: an exploded view has been shown in order to better view the interior of the device;

FIG. 3 shows the same device, in two versions, placed on an injection platform above a row of two eggs;

DETAILED DESCRIPTION OF THE EMBODIMENTS

Figure 4:
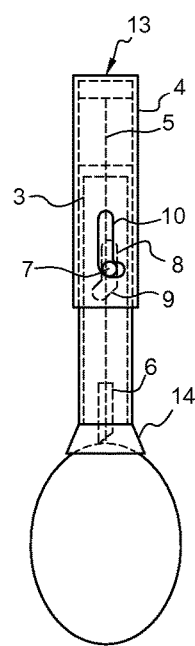
FIG. 4 shows a profile view of an injection device according to the embodiment shown in FIG. 1, in another configuration.

FIGS. 1 and 2 show a first embodiment of an in-ovo injection device 1 according to the invention including a guide member 2 formed by an inner casing 3 covered by an outer casing 4, both of which are substantially cylindrical in shape. The outer casing 4 is fastened to an injection needle 5 which passes through a trocar 6 on which a bonding stud 7 connected to the two casings, the inner casing 3 and the outer casing 4, is mounted. A grooving, known as a first grooving 8, is made on the inner casing 3 through the entire thickness thereof and includes a bend, referred to as a first bend 9, which extends at one of the ends thereof. Another grooving, known as a second grooving 10, is made on the outer casing 4 through the entire thickness thereof and includes a bend, referred to as a second bend 11, which extends at one of the ends thereof. The two bends 9 and 11 are positioned on the same side—on the respective grooving thereof—of the guide member 2.

The bonding stud 7, which is mounted on the trocar 6 in which the injection needle 5 slides, passes through the two groovings 8 and 10 and ends in a bevelled head which slides on the edges of the second grooving by the outside face of the outer casing, referred to as outer edges of the second grooving.

The first bend 9 is configured such that the slot thereof communicates with the slot of the second grooving 10, and the bonding stud 7 passes through both the first bend 9 and the second grooving 10 when the inner casing 3 is set in motion on the inner casing 4 in a first area of displacement of the guide member 2. The first area of displacement is partially shown in FIGS. 6 and 7. Similarly, the second bend 11 is configured such that the slot thereof communicates with the slot of the first grooving 8, and the bonding stud 7 passes through the second bend 11 and the first grooving 8 when the inner casing 3 is set in motion on the inner casing 4 in a second area of displacement of the guide member 2. The second area of displacement is partially shown in FIGS. 1, 2, 3, 4 and 5.

The outer casing 4 comprises a bottom 13 which closes a first end of the guide member, and which is fastened to an injection needle 5. The inner casing 3 comprises a cup 14 placed at the second end of the guide member, and shaped so as to cover a chicken egg.

To perform an injection into a chicken egg, the device 1 according to the invention mounted on an injection platform 15 is at rest in a first configuration in which the bonding stud 7 is housed inside the second bend 11 and the injection needle 5 is fully retracted. An egg is brought beneath the device 1 using a conveyor and once it is positioned beneath the injection platform 15 facing the device 1, the platform 15 is lowered such that the cup 14 covers the top part of the egg.

Figure 5:
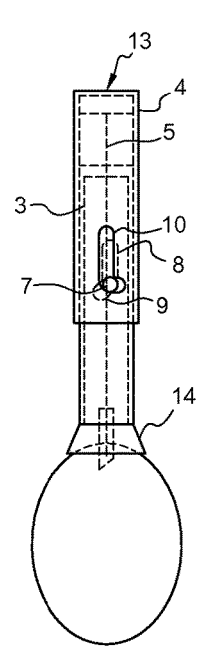
FIG. 5 shows a profile view of an injection device according to the embodiment shown in the preceding figures, in another configuration.
Figure 7:
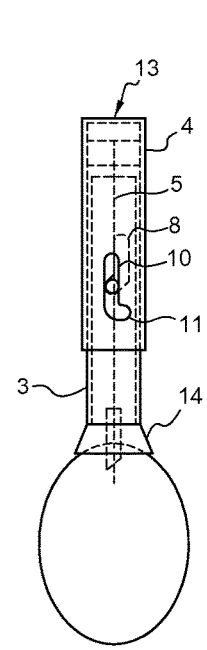
FIG. 7 shows a profile view of an injection device according to the embodiment shown in the preceding figures, in another configuration.
Figure 8:
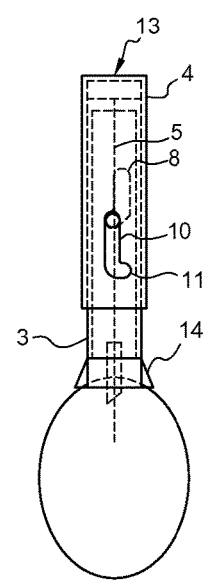
FIG. 8 shows a profile view of an injection device according to the embodiment shown in the preceding figures, in another configuration.

In order to perform the injection of a composition into the egg by compressing the guide member 2, which initially occupies a first configuration shown in FIG. 4, the following steps are carried out:

an egg is placed beneath the guide member 2 which occupies (FIG. 4), at rest, a first configuration wherein the bonding stud 7 is housed inside the second bend 11 and the needle 5 is fully retracted;

the top part of the egg is covered by the cup 14;

once contact has been made, the guide member 2 is compressed against the egg so as to cause the outer casing 4 to slide relative to the inner casing 3 with displacement of the bonding stud 7 inside the first grooving 8 (see FIG. 5);

the compression of the guide member 2 is maintained until the egg is punctured and until the guide stud 7 is blocked (see FIG. 6) in the first bend 9 in order to block the displacement of the trocar 6; and the compression is continued in order to induce the sliding of the bonding stud 7 inside the second grooving 10 and subsequently, the lowering of the needle 5 (see FIG. 7) until the guide member 2 is in the injection configuration (see FIG. 8).

Figure 6:
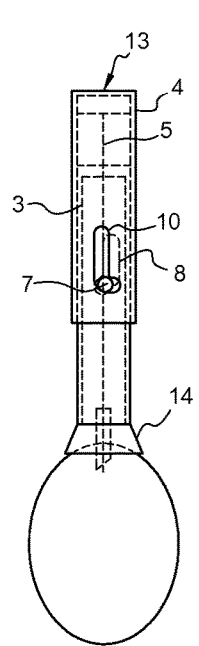
FIG. 6 shows a profile view of an injection device according to the embodiment shown in FIGS. 1 to 3, in another configuration.

The displacement of the bonding stud 7 inside the first grooving 8 results, at the end of its path, in the sliding of the bonding stud 7 inside the first bend 9. The successive steps of this sliding of the bonding stud 7 in the first bend 9 are shown in FIG. 5 to FIG. 7, which causes the trocar 6 to rotate. This rotation of the trocar 6 results in reducing the transverse downwards bearing of the trocar which has already punctured the egg. This rotation of the trocar 6 thus releases the pressurise applied to the egg, which prevents the shell of the egg from being broken or cracked.

Figure 13:
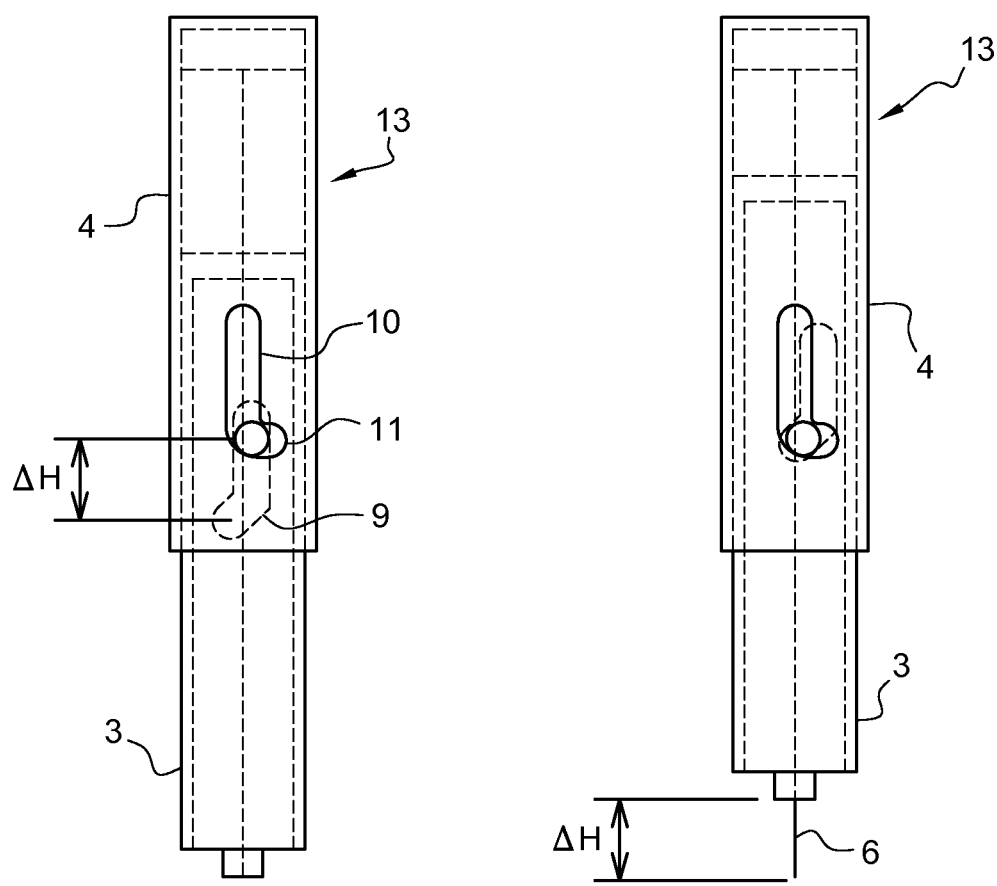
FIG. 13 shows the guide member and the trocar and the means for connecting the trocar to the guide member of the device according to the invention in two end configurations I and II.

FIG. 13 shows how such a device allows the penetration depth of the trocar to be precisely defined in order to avoid the drawbacks described hereinabove. The height ΔH between the first bend 9 of the first grooving 8 and the second bend 11 of the second grooving 10 along the longitudinal axis, and when the injector is in the resting configuration (configuration I) corresponds to the maximum depth of penetration of the trocar inside the egg: that is to say the maximum distance substantially between the projection of the rims of the cup 14 on the axis of the trocar (in this case it is the lower end of the guide member that is shown) and the end of the trocar 6, when the injector is in a configuration known as a puncturing configuration (configuration II), this puncturing configuration also being shown in FIG. 6.

Figure 9:
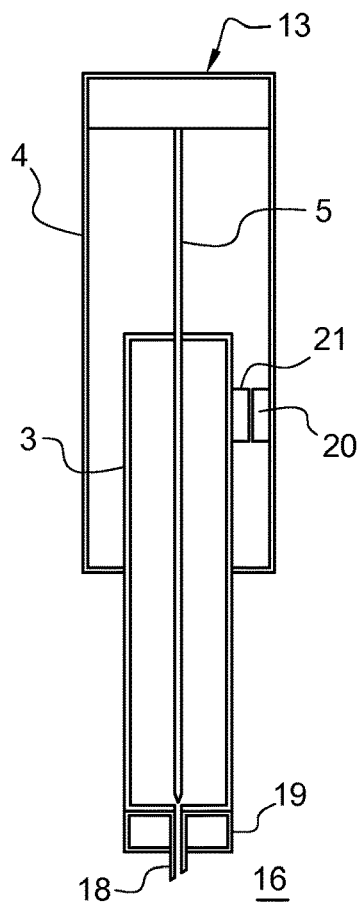
FIG. 9 shows a sectional view of another embodiment according to the invention.

Another embodiment of the in-ovo injection device according to the invention is shown, namely the device 16 in FIG. 9. Similarly to the device 1 of the embodiment described hereinabove in the context of the invention, this device 16 includes a guide member 17 formed by an inner casing 3 covered by an outer casing 4, both having a substantially cylindrical shape. The outer casing 4 comprises a bottom 13 which closes a first end of the guide member, and which is fastened to an injection needle 5 which passes through a trocar 18. The trocar 18 is fastened to a cup 19 placed at the second end of the guide member, and shaped so as to cover a chicken egg. A first magnet 20 is fastened to the inside face of the outer casing 4, and facing a second magnet 21 which is itself fastened to the outside face of the inner casing 3 in a configuration of the guide member known as the puncturing configuration, shown in FIGS. 9 and 10.

Figure 10:
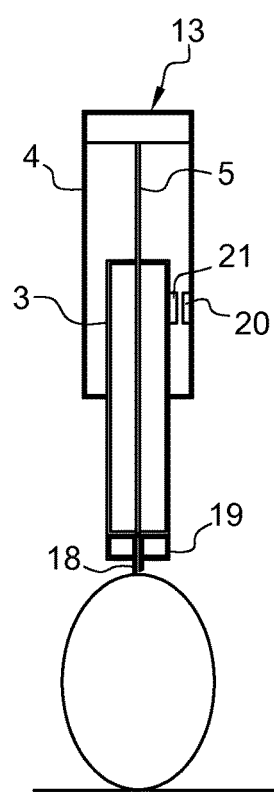
FIG. 10 shows a sectional view of the device shown in FIG. 9 positioned on an egg.
Figure 11:
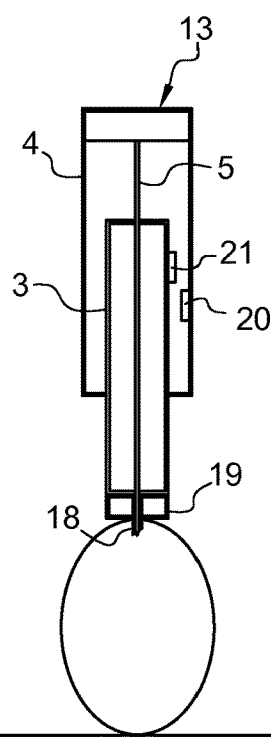
FIG. 11 shows a sectional view of the device shown in FIG. 10 in another configuration.
Figure 12:
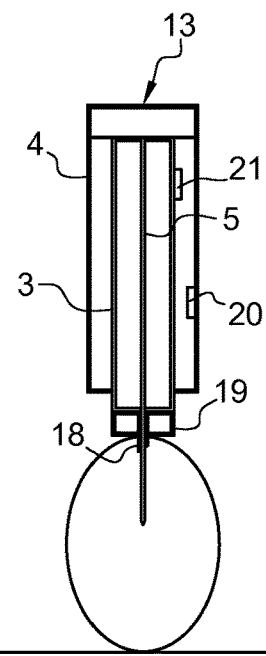
FIG. 12 shows a sectional view of the device shown in FIGS. 10 and 11, in another configuration.

In order to perform the injection of a composition into the egg by compressing the guide member 2, which initially occupies the puncturing configuration shown in FIG. 9 or 10, the following steps are carried out:

the trocar 18 is positioned on the top part of an egg;

the guide member 2 is pressurised on the top part of the egg which occupies the puncturing configuration wherein said first and second magnets 20, 21 are positioned facing one another in the guide member until the egg is punctured;

compression is maintained until the magnetisation between the first magnet and the second magnet is broken (FIG. 11), and subsequently until the sliding of the outer casing relative to the inner casing, which results in the lowering of the trocar into the punctured egg until the cup is positioned on the top part of said egg; and the guide member is further compressed to cause the needle to be lowered until the guide member occupies the injection configuration (FIG. 12).

The invention claimed is:

1. A device to inject a composition into an egg, comprising:

a trocar comprising a tubular body and an injector mounted such that the injector slides at least partially inside the tubular body of the trocar between a first position in which an injection end of the injector is fully retracted inside the tubular body, and a second position in which the injection end of the injector projects outside of the tubular body of the trocar;

a guide member comprising an outer casing secured to the injector and an inner casing configured to move in translation inside the outer casing, the inner casing being connected to the trocar and comprising a cup configured to bear on a top part of the egg;

a first locking member configured to block a movement of the trocar; and a second locking member configured to block a movement of the injector in which the injector is retracted inside the trocar.

2. The device according to claim 1, wherein the guide member comprises:

a first groove on an outer face of the inner casing and a second groove on an inner face of the outer casing, the first and the second grooves extend longitudinally in the guide member and substantially face one another, the first groove comprises the first locking member comprising a first bend positioned at one of two ends of the first groove, the second groove comprises the second locking member comprising a second bend positioned at one of two ends of the second groove;

a bonding stud mounted to slide inside both the first groove and the second groove;

wherein the first bend is configured to block the sliding of the bonding stud inside the second groove and configured to bear against one end of the second groove; and wherein the second bend is configured to block the sliding of the bonding stud inside the first groove and configured to bear against one end of the first groove.

3. The device according to claim 2, wherein the first groove passes through the inner casing and the bonding stud comprising first and second ends, the bonding stud is fastened by the first end to the trocar and passes through the first groove while being housed inside the second groove via the second end.

4. The device according to claim 3, wherein the bonding stud penetrates and passes through the second groove, the bonding stud comprising a head configured to engage outer edges of the second groove.

5. The device according to claim 2, further comprising a third locking member configured to block a displacement of the injector in an injection configuration of the guide member wherein the injector projects outside of the trocar; and wherein the third locking member is at an end of the second groove opposite the end which includes the first bend.

6. An injection method implementing the device according claim 5, comprising:
   placing the egg beneath the guide member in a first configuration wherein the bonding stud is housed inside the second bend and the injector is fully retracted;
   compressing the guide member and subsequently sliding the outer casing relative to the inner casing with a displacement of the bonding stud in the first groove until the cup is positioned on the top part of an egg according to a second configuration of the guide member;
   continuing the compression of the guide member in order to puncture a shell of the egg by the trocar; and
   maintaining the compression until the egg is punctured and until the bonding stud is blocked in the first bend in order to block the displacement of the trocar; and
   compressing the guide member further to cause the bonding stud to slide inside the second groove and to lower the injector until the device is in the injection configuration.

7. The device according to claim 1, wherein the second locking member comprises a first magnet positioned on an outer face of the inner casing and a second magnet positioned on an inner face of the outer casing, the first and second magnets being positioned facing one another in the guide member in a puncturing configuration of the guide member.

8. The device according to claim 7, wherein the first locking member is formed by a rigid connection of the trocar to the cup.

9. An injection method implementing the device according to claim 7, the device further comprising a third locking member configured to block a displacement of the injector in an injection configuration of the guide member wherein the injector projects outside of the trocar, comprising:
   positioning the trocar on the top part of the egg;
   compressing the guide member on the top part of the egg to the puncturing configuration wherein said first and second magnets are positioned facing one another in the guide member until the egg is punctured;
   maintaining the compression of the guide member until a magnetization between the first magnet and the second magnet is broken, and subsequently until the outer casing slides relative to the inner casing to lower the trocar into the punctured egg until the cup is positioned on the top part of the egg; and
   further compressing the guide member to lower the injector until the device is in the injection configuration.

10. The device according to claim 1, further comprising a third locking member configured to block a displacement of the injector in an injection configuration of the guide member wherein the injector projects outside of the trocar.

11. The device according to claim 10, wherein the outer casing comprises a bottom and the third locking member comprises said bottom, a border of the inner casing configured to abut against the bottom in the injection configuration.

12. The device according to claim 1 to inject a liquid solution, wherein the injector is an injection needle.

* * * * *